(12) United States Patent
Fehling

(10) Patent No.: US 7,182,730 B2
(45) Date of Patent: Feb. 27, 2007

(54) ANAL RETRACTOR

(75) Inventor: Guido Fehling, Karlstein (DE)

(73) Assignee: Fehling AG, Reinach (CH)

( * ) Notice: Subject to any disclaimer, the term of this patent is extended or adjusted under 35 U.S.C. 154(b) by 0 days.

(21) Appl. No.: 11/079,410

(22) Filed: Mar. 14, 2005

(65) Prior Publication Data

US 2005/0203347 A1 Sep. 15, 2005

(30) Foreign Application Priority Data

Mar. 12, 2004 (DE) .................. 10 2004 012 109

(51) Int. Cl.
*A61B 1/31* (2006.01)
(52) U.S. Cl. ...................... 600/224; 600/210
(58) Field of Classification Search ............... 600/208, 600/210, 214, 215, 217, 219, 222, 234
See application file for complete search history.

(56) References Cited

U.S. PATENT DOCUMENTS

| | | | | |
|---|---|---|---|---|
| 151,228 A | * | 5/1874 | Knaffl ...................... 600/224 |
| 1,157,202 A | * | 10/1915 | Bates et al. ............... 600/208 |
| 2,070,670 A | * | 2/1937 | Marshall ................... 600/218 |
| 2,083,573 A | | 6/1937 | Morgan |
| 2,384,304 A | * | 9/1945 | Helfrick ................... 600/233 |
| 2,594,086 A | * | 4/1952 | Smith ....................... 600/228 |
| 2,893,378 A | * | 7/1959 | Cooper ..................... 600/233 |
| 4,130,113 A | * | 12/1978 | Graham .................... 600/224 |
| 5,345,927 A | * | 9/1994 | Bonutti ..................... 600/207 |
| 5,377,667 A | * | 1/1995 | Patton et al. ............. 600/184 |
| 5,505,690 A | * | 4/1996 | Patton et al. ............. 600/210 |
| 5,681,265 A | | 10/1997 | Maeda |
| 6,342,036 B1 | * | 1/2002 | Cooper et al. ............ 600/224 |
| 6,354,995 B1 | * | 3/2002 | Hoftman et al. .......... 600/219 |
| 6,468,207 B1 | * | 10/2002 | Fowler, Jr. ................ 600/233 |

* cited by examiner

*Primary Examiner*—Cris L. Rodriguez
*Assistant Examiner*—Patrick J. Kilkenny
(74) *Attorney, Agent, or Firm*—Akerman Senterfitt; Stephan A. Pendorf; Peter A. Chiabotti

(57) ABSTRACT

An anal retractor includes four retractor valves (48), which are offset 90° relative to each other and can be moved radially apart from each other. For this the four retractor valves (48) are guided by sleds (30) in radial guide slots (14) of a base plate (10). For movement of the sleds (30) guide bolts (36) extend through the radial guide slots (14) of the base plate (10) and spiral shaped actuating slots (24) of a rotor plate (20), which is rotatable relative to the base plate (10).

14 Claims, 6 Drawing Sheets

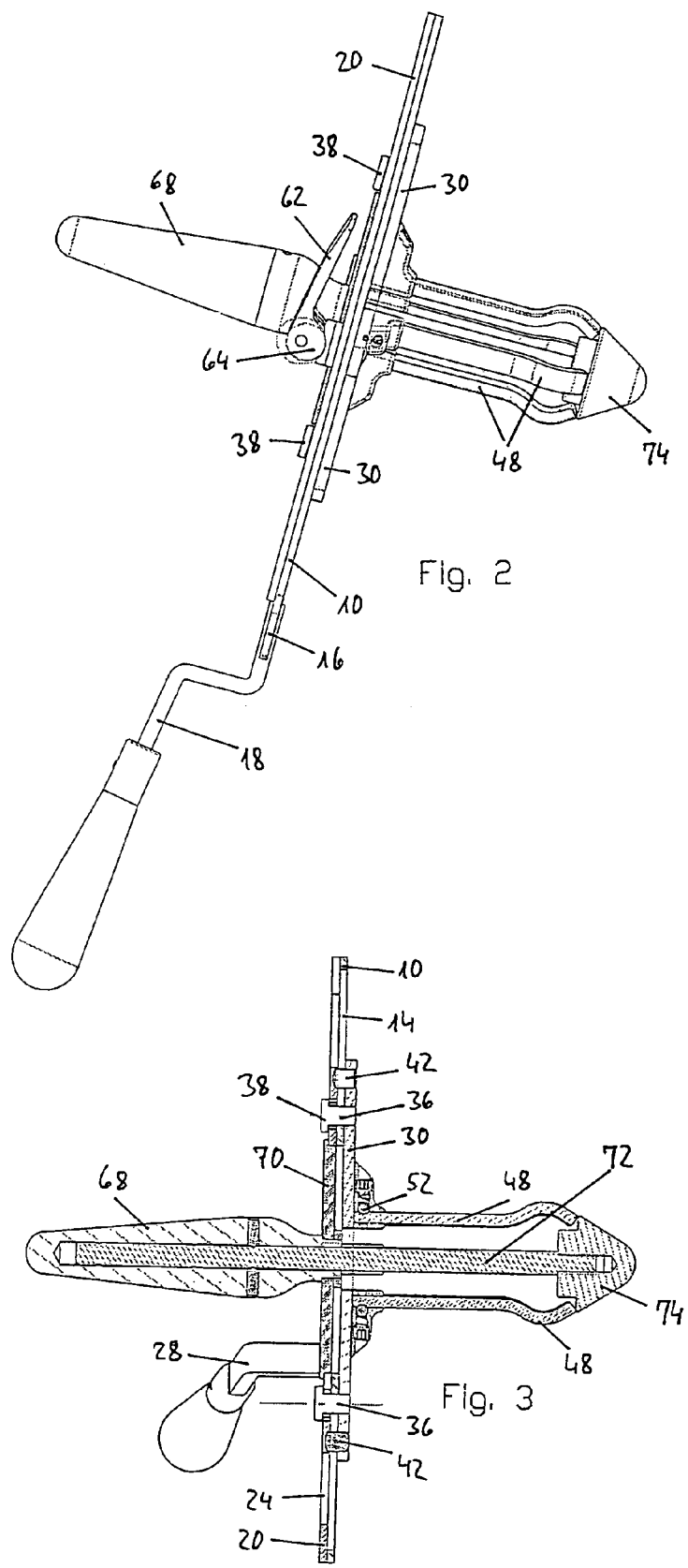

ANAL RETRACTOR

BACKGROUND OF THE INVENTION

1. Field of the Invention

The invention concerns an anal retractor with retractor valves guided for movement apart.

2. Related Art of the Invention

Anal retractors are used in order to dilate the anal canal for medical interventions and examinations. These anal retractors include retractor valves, which are introduced into the anal canal and then are moved apart for dilation of the anal canal.

In one known embodiment two retractor valves are provided, which are spread apart using a scissors grip. Therewith only a comparatively small dilation of the anal canal is possible. Further, an anal retractor with two retractor valves is known, in which the one retractor valve is displaceable on a guide rail provided upon the other retractor valve. Therewith the retractor blades can, on the one hand, be spread further apart, the spreading of the anal canal occurs however only in diametrically opposed directions, so that the access cross-section is not optimally enlarged. Finally, an anal retractor is known in which two retractor valves can be moved apart via a scissors grip and wherein a third retractor valve is provided pivotable about a plane perpendicular to the pivot axis of the scissors grip. The three retractor valves produce a larger access cross-section of the dilated anal canal. The access cross-section is however asymmetric in this case, and is essentially determined by the diametric spreading movement of the scissors grip.

SUMMARY OF THE INVENTION

The invention is concerned with the task of providing an anal retractor which makes possible an improved access for medical examination and intervention.

This task is inventively solved by the anal retractor with retractor valves guided for movement apart, comprising: a base plate (10) with a central access opening (12), at least three guide slots (14) in the base plate (10) extending radially outside of the opening (12) and angularly offset relative to each other, retractor valves (48) radially displaceable in the guides (14), projecting essentially perpendicularly from the base plate (10) in the distal direction, and actuating means (20, 24) for radial displacement of the retractor valves (48) in the guide slots (14).

Advantageous embodiments and further developments of the invention are set forth in the dependent claims.

In the inventive anal retractor the retractor valves are guided radially slideable in a base plate. Thereby it becomes possible to provide a greater number of retractor valves symmetrically about a central free opening of the base plate and accordingly it becomes possible to dilate the anal canal symmetrically with optimal cross-section. If three retractor valves are employed, which are offset radially at an angle of 120° relative to each other, then there results a triangular widening of the anal canal. An optimal embodiment is produced using four retractor valves, which are radially displaceable in guides offset by 90° relative to each other. The four retractor valves produce an approximately square access cross-section of the dilated anal canal, which provides the doctor with a greater freedom of movement. More than four retractor valves are possible in accordance with the invention; however, more retractor valves do not provide any substantial improvement in the access cross-section, but lead rather to a greater coverage of the wall of the anal canal by the retractor valves.

In one advantageous embodiment the retractor valves are guided in the radial guides via sleds. It is in particular also possible to releasably or exchangeably secure the retractor valves to the sleds, wherein in particular a locking connection can be provided. It is possible thereby to design the anal retractor with one base or fundamental instrument, which can be equipped with suitable retractor valves depending upon the respective intended application.

In a preferred embodiment the retractor valves and in particular the sleds carrying the retractor valves are moved in the radial guides by a rotor plate. The retractor valves or, as the case may be, the sleds carrying them, have guide bolts, which extend through the radial guides of the base plate and the spiral shaped actuating slots of the rotor plate, transecting these radial guides. If the base plate and the rotor plate are rotated concentrically to each other, then the crossing points of the radial guide slots and the spiral actuating slots, in which the guide bolts are located, move radially outward and move the retractor valves radially apart. Thereby the retractor valves can be spread apart exactly symmetrically to each other and be moved apart with a sensitive tactile application of force.

In a preferred embodiment the base plate and the rotor plate can be clamped to each other in their respective rotation positions via a clamping device, in order to arrest the retractor valves in their respective spread position.

In order to be able to introduce the anal retractor as painless as possible and without tissue damage, a mandrel is preferably provided, which can be seated centrally in the base plate. The mandrel projects distally beyond the base plate and exhibits a distal truncated conical end piece. When the retractor valves are slid to their radial innermost position, the distal free ends of the retractor valves engage behind the proximal edge of the conic end piece, and are covered by the end piece when the mandrel is introduced into the anal canal with the retractor valves lying there-against. As soon as the retractor valves are positioned in the anal canal, these are radially moved apart, so that the mandrel, together with its conical end piece, can be withdrawn proximally.

In one useful embodiment the mandrel includes an axial shaft, which carries the distal end piece. This shaft is mounted axially displaceable in a proximal mandrel handle or grip. Thereby the axial position of the end piece can be adjusted relative to the base plate and be adapted to the respective employed retractor valves.

BRIEF DESCRIPTION OF THE DRAWING

In the following the invention will be described in greater detail on the basis of the illustrated embodiment shown in the figures. There is shown FIG. 1 an axial top view onto the anal retractor from the distal side, FIG. 2 a side view of the anal retractor, FIG. 3 an axial segment along the section line A—A in FIG. 1, FIG. 4 a top view upon the base plate, FIG. 5 a top view upon the rotor plate, FIG. 6 a perspective view of a retractor valve with pusher, FIG. 7 an axial segment of the retractor valve with pusher according to FIG. 6 and FIG. 8 an axial section through the mandrel.

DETAILED DESCRIPTION OF THE INVENTION

Figure 1:
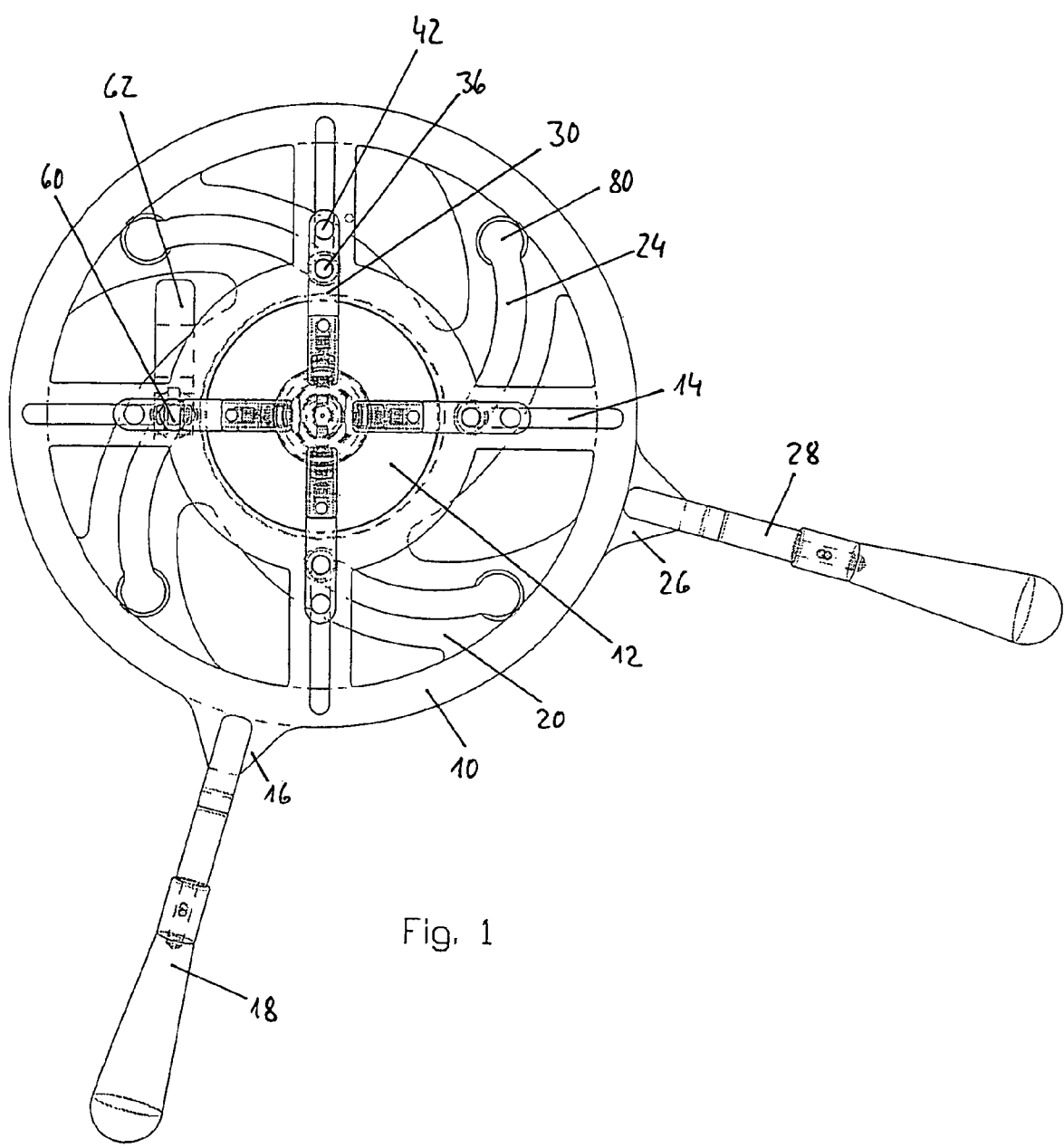
Figure 4:
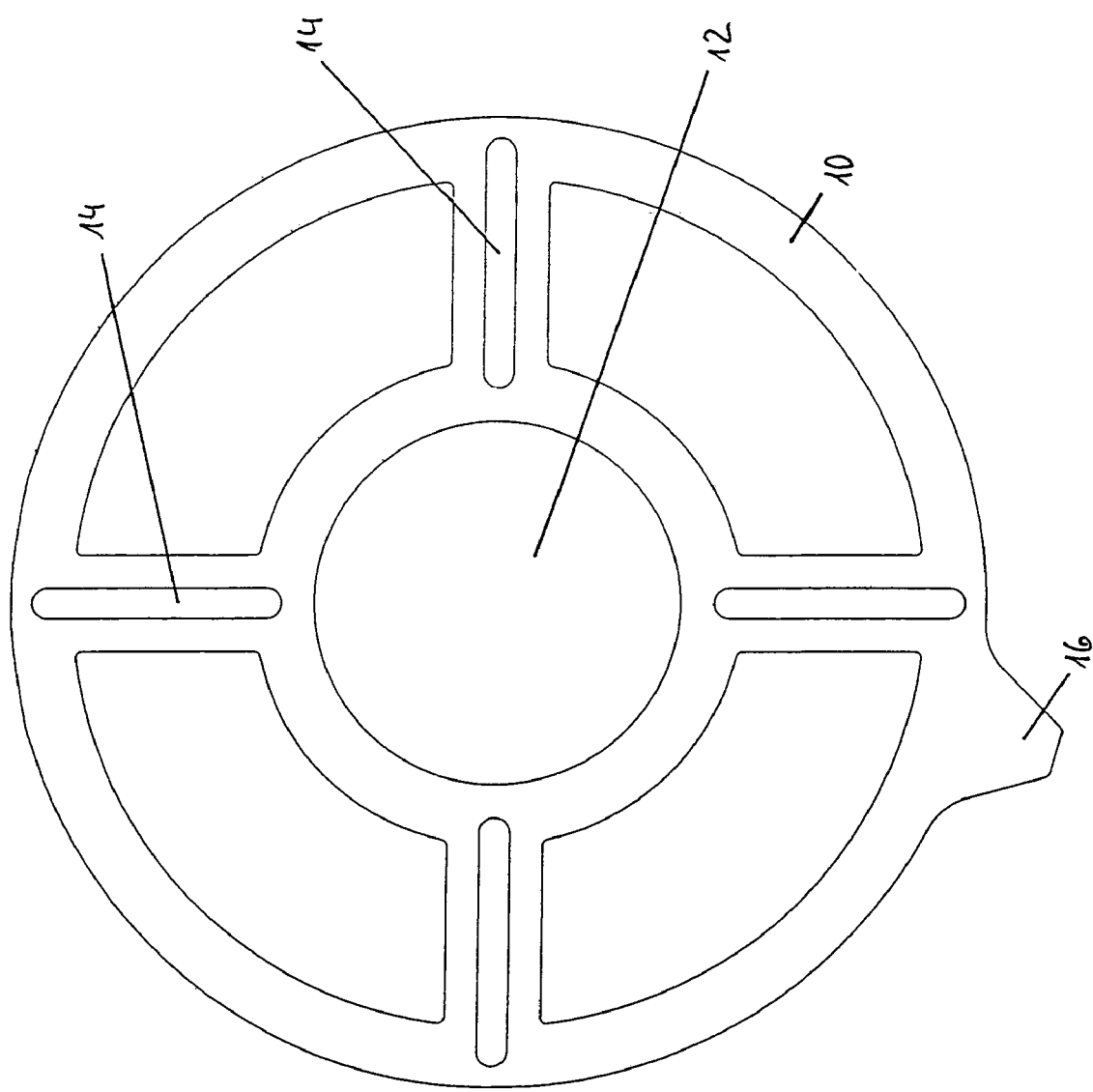

The anal retractor includes a base plate 10, which is shown in detail in FIG. 4. The base plate 10 has the shape of a circular disk with a central circular free opening 12. The opening 12 defines the cross-section of free access and exhibits a diameter of, for example, 60 mm. Radial guides run outside of the opening 12, in the form of guide slots 14 extending through the base plate 10. In the shown embodiment four guide slots 14 are provided, which are offset by 90° relative to each other with equal angular distribution. On it's circumference the base plate 10 exhibits a radially extending lobe 16, to which a radial projecting grip or handle lever 18 is secured, for example, by welding.

Figure 5:
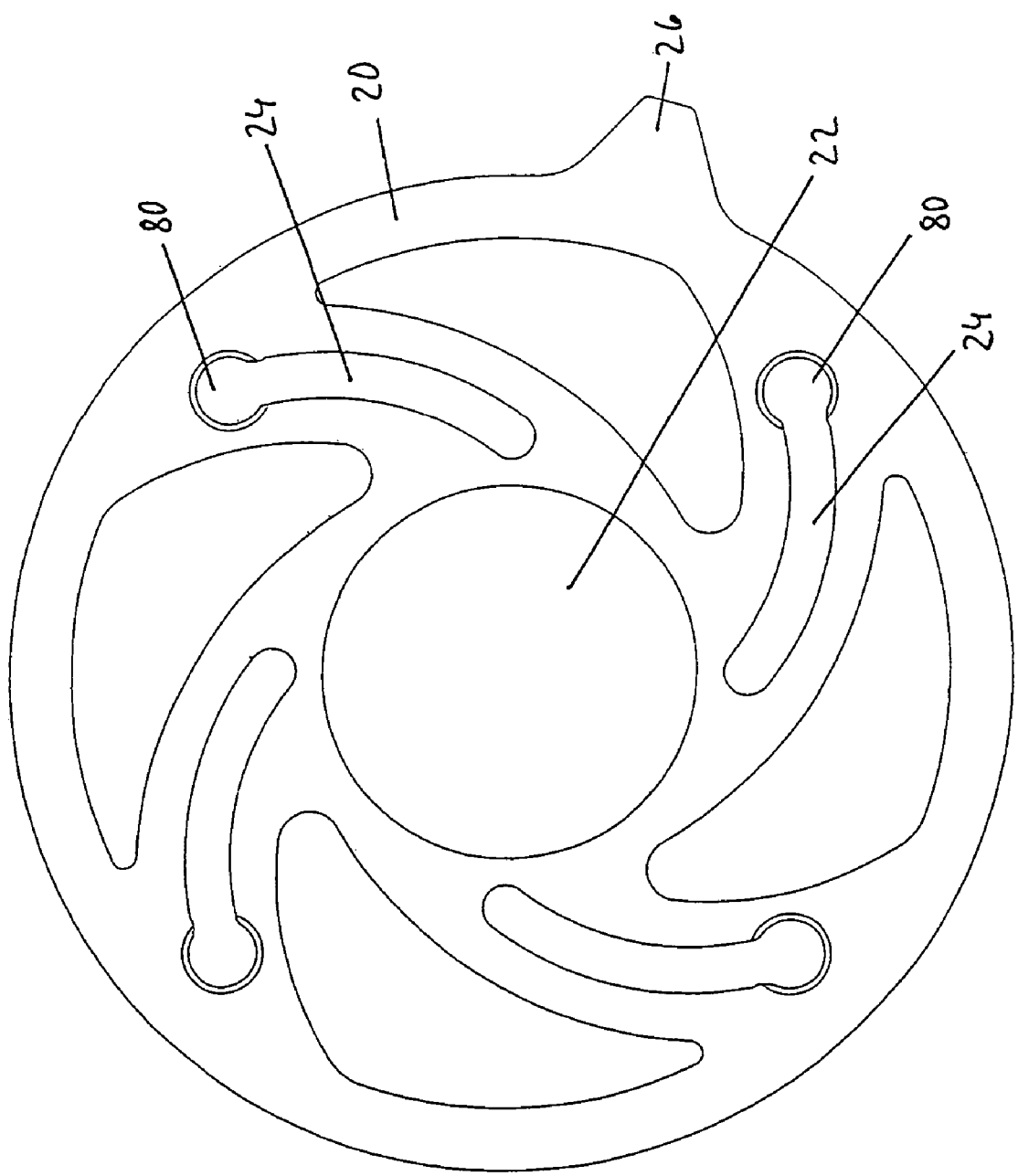

A rotor plate 20 lies against the proximal surface of the base plate 10, which is shown separately in detail in FIG. 5. The rotor plate 20 likewise has the shape of a circular disk, of which the outer diameter essentially corresponds with the outer diameter of the base plate 10. In the center the rotor plate 20 likewise exhibits a free opening 22 with circular cross-section, of which the diameter is at least the same as the diameter of the central opening of the base plate 10. Actuating slots 24 extend through the rotor plate 20 outside of the opening 22. The actuating slots 24 run spiral-shaped towards outwards. The number and arrangement of the actuating slots 24 corresponds to the guide slots 14 of the base plate 10. In the shown illustrated embodiment four actuating slots 24 are provided respectively offset by 90.degree. relative to each other. The inner end of the guide slot 14 and the actuating slot 24 lies on the same radius and in the same manner the outer ends of the guide slots 14 and actuating slots 24 lie on the same radius. Due to the spiral shaped curvature of the actuating slot 24 its outer end is displaced by approximately 45.degree. in comparison to the inner end. The rotor plate 20 exhibits on its outer circumference likewise a radial projecting lobe 26, on which a radial projecting handle lever 28 is secured, for example by welding.

Figure 6:
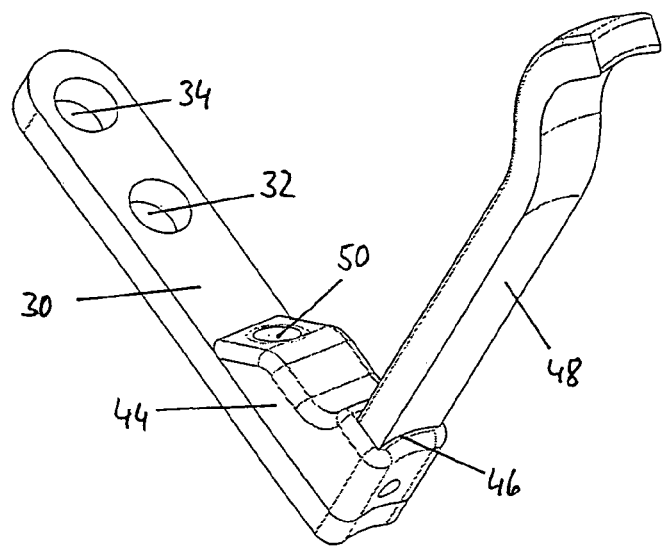
Figure 7:
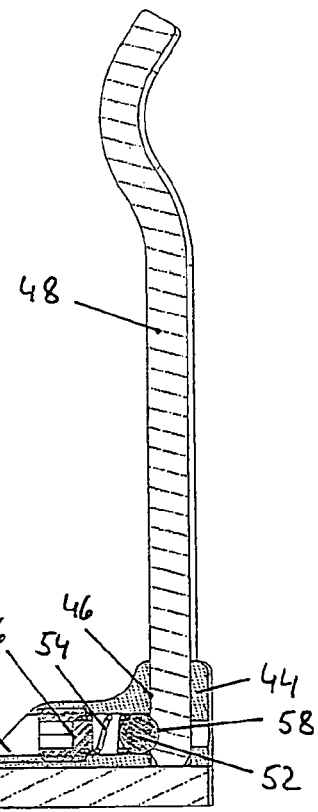

Distally upon the base plate 10 there are seated respectively sleds 30 associated with the guide slots 14, which are shown as individual components in FIGS. 6 and 7. The sleds 30 have the shape of a flat elongated plate, which lies in radial direction parallel upon the guide slots 14. The sleds 30 exhibit two boreholes 32 and 34 spaced apart in the radial direction. The diameter of the bore holes 32 and 34 corresponds to the breadth of the guide slot 14. In the radial inner bore 32 guide bolt 36 is rigidly secured. The guide bolt 36 extends through the bore 32, the guide slot 14 of the base plate 10 and the respective actuating slot 24 of the thereagainst lying rotor plate 20. Upon the proximal side, the widened head 38 of the guide bolt 36 overlaps with the actuating slot 24, whereby the rotor plate 20 is held to the base plate 10. In the radial outer bore 34 of the sled 30 a mounting pin 42 is seated, which is held non-releasably in the sled 30 and engages in the guide slot 14.

A block 44 is formed on the radial central end of the sled 30. The block 44 exhibits a receptacle pocket 46, which is provided close to the radial inner end of the sled 30, which leads from the distal side perpendicular to the sled 30 in the block 44 and has the cross-sectional shape of a slit running perpendicular to the longitudinal direction of the sled 30. In the receptacle pocket 46 there are seated respectively exchangeable retractor valves 48. For this, a borehole 50 is provided in the block 44, which runs parallel to the surface and longitudinal direction of the sled 30 and runs until it reaches the receptacle pocket 46. In this borehole 50 a detent ball 52 is introduced which ball projects with its circumference into the receptacle pocket 46 and is pretensioned by a compression spring 54. The compression spring is supported with its end opposite to the detent ball 52 against an adjustment screw 56, which is screwed into an inner threading of the bore 50, and by means of which the pretensioning of the compression spring and therewith the detent ball 52 can be adjusted. The retractor valve 48 exhibits on its end engaging the receptacle pocket 46 a detent recess 58, in which the detent ball 52 is snapped-in under tension, in order to arrest the retractor valve 48 in the receptacle pocket 46. In this manner the retractor valve 48 can be locked in place by the simple insertion into the receptacle pocket 46 on the sled 30. Likewise the retractor valve 48 can again be removed from the sled 30, in that the retractor valve 48 is pulled out against the locking force of the detent ball 52.

If the base plate 10 and the rotor plate 20 are rotated relative to each other using the grip levers 18 and 28, then the crossing points of the radial guide slots 14 and the spiral shaped actuating slots 24 move radially. Since the guide bolts 36 of the sled 30 pass through in these crossing points of both the respective guide slots 14 as well as the respective actuating slots 24, the guide bolts 36 move radially in the guide slot 14. Since the sled 30 with the guide bolts 36 and the mounting pins 42 is guided respectively in the guide slots 14, the sleds 30 are moved radially along the guide slot 14 by the rotation of the base plate 10 and rotor plate 20 relative to each other. Therewith the distal separated retractor valves 48 of the four sleds 30 can be moved radially towards and apart from each other.

In one of the sleds 30 the guide bolt 36 is, in addition to its guide function, also designed to be a tensioning or spring bolt 60. On the proximal end of the tensioning bolt 60 projecting beyond the rotor plate 20 there is, in place of the head bolt 38, an eccentric lever 62 mounted pivotable about an axis eccentric to the perpendicular axis of the tensioning bolt 60. The eccentric lever 62 exhibits in the area of the tensioning bolt 60 an eccentric cam 64, which is supported upon the surface of the rotor plate 20. If the eccentric lever 62 is pivoted with its free lever grip from the rotor plate 20, then the eccentric cam 64 provides the tensioning bolt 60 with a small amount of axial play. On the basis of this axial play the sled 30 can move and the base plate 10 and the rotor plate 20 can be rotated relative to each other. If the eccentric lever 62 is pivoted against the rotor plate 20 into the clamping or tensioning position, as this is shown in FIG. 2, then the eccentric cam 64 supports itself against the rotor plate 20 and pulls the tensioning bolt 60 axially in the proximal direction. Therewith the base plate 10 and the rotor plate 20 are clamped and tensioned between the sled 30 and the eccentric cam 64 of the eccentric lever 62, so that the rotor plate 20 and the base plate 10 can no longer be rotated relative to each other and the retractor valves 48 are arrested or locked in their respective position.

Figure 8:
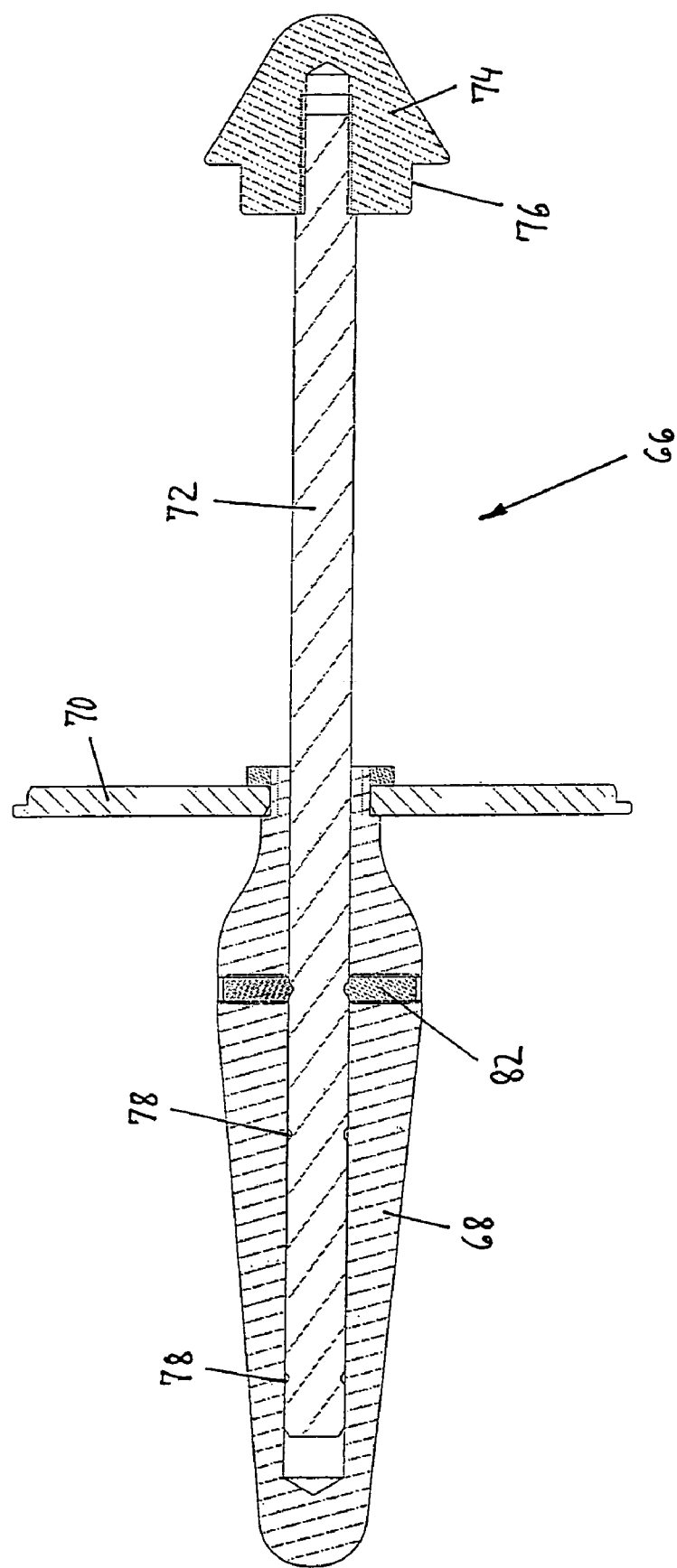

In the central opening 12 of the base plate 10 and 22 of the rotor plate 20 a mandrel 66 can be introduced, which is shown as a separate part in FIG. 8.

The mandrel 66 exhibits a proximal mandrel grip 68, which is screwed into a disk shaped support plate 70. The outer diameter of the support plate corresponds to the diameter of the central opening 22 of the rotor plate 20, so that the support plate 10 can be seated in this opening 22, whereby it supports itself with its circumferential shoulder upon the circumference of the opening 22. In the mandrel grip 68 there is inserted axially a shaft 72, which projects distally out of the mandrel grip 68. On the distal end of the shaft 72 an end piece 74 is seated, for example is screwed on. The end piece 74 has the shape of a cone with truncated distal tip, which widens in the proximal direction. On the proximal end the end piece 74 exhibits a circumferential step 76, which is overlapped by the proximal outer edge of the end piece 74.

The shaft 72 exhibits on its area engaging in the mandrel grip 68 axially spaced apart detent grooves or recesses 78. In these detent recesses radial detent pieces 82 can engage, which are incorporated in the mandrel grip 68. Thereby it becomes possible to ratchet the shaft 72 to project with different axial lengths from the mandrel grip 68. Thereby it is determined how far the end piece 76 is spaced apart distally from the base plate 10 and the sled 30, when the mandrel 66 with its support plate 70 is seated in the rotor plate 20.

For the employment of the anal retractor, the retractor valves 48 suitable for the respective application are locked in into the sleds 30. The mandrel 66 is seated with its support plate 70 in the opening 22 of the rotor plate 20. In the case of released eccentric levers 62 the base plate 10 and the rotor plate 20 are so rotated that the sleds 30 are pushed radially inwards. The free distal ends of the retractor valves 48 in this case lie against the circumferential step 76 of the end piece 74 of the mandrel 66. The end piece 74 is so adjusted by displacement and locking of the shaft 72 in the mandrel grip 68, that the free distal ends of the retractor valves 48 lie in the circumferential step 76 axially against the end piece 74 and are covered by its proximal outer circumference.

Now the mandrel 66 can be introduced into the anal canal of the patient. Due to the truncated conical end piece 74, it becomes possible to introduce the device with minimal pain. Since the end piece 74 overlaps the free distal ends of the retractor valves 48, tissue damage in the anal canal during introduction of the retractor valves 48 is prevented.

As soon as the mandrel 66 is positioned with the retractor valves 48 in the anal canal, the base plate 10 and the rotor plate 20 are rotated by means of the grip lever 18 and 28, so that the sleds 30 with the retractor valves 48 are moved radially outwards. Therewith the retractor valves 48 come radially out of the area of the end piece 74 and the mandrel 66 with the end piece 74 and the support plate 70 can be extracted proximally through the opening 12 and 22. The openings 12 and 22 now form the free access cross-section of the anal retractor. By the further rotation of the base plate and rotor plate 20 relative to each other now the sleds 30 with the retractor valves 48 are moved further radially outwards, in order to widen the anal canal. If the anal canal is sufficiently dilated, then the eccentric lever 64 is pivoted against the rotor plate, in order to clamp the rotor plate 20 and the base plate 10 to each other and arrest the retractor valves 48 in their position.

The retractor valves 48 preferably exhibit a small width of approximately 6 mm. If the retractor valves 48 are moved out to their maximal separation, which corresponds to a diameter of 60 mm of the opening 12 and 22, there results thereby an approximately square access cross-section of the anal canal with a 60 mm diagonal, wherein the four retractor valves 48 only cover a surface of the wall of the anal canal with a breadth of 24 mm in the circumference direction. Therewith the greatest part of the wall of the anal canal is exposed, so that examination and intervention in this area of the anal canal can be carried out. For examination and intervention deeper into the bowel or intestinal area, a greater moveability of the instrument is possible, since the free-lying areas of the wall of the anal canal not covered by the rigid retractor valves 48 can yield to instruments lying there-against.

In an advantageous embodiment the actuating slots 24 respectively exhibit segments 80 which are widened to the extent that the head 38 of the guide bolt 36 can pass there-through. If the base plate 10 and the rotor plate 20 are so rotated relative to each other that the guide bolt 36 comes into the widened segment 80 of the actuating slot 24, then the guide bolt 36 can be extracted through the widened segment 80, whereby the base plate 10 and the rotor plate 20 are no longer held together. The base plate 10 and the rotor plate 20 can, in this manner, be separated and reassembled without requiring assistance of tools. The widened segments 80 are preferably located at the radial outer ends of the actuating slots 24, so that the separation occurs in a spread position of the sleds 30 and the retractor valves 48, which is not reached during the use of the anal retractor.

10 base plate
12 opening
14 guide slot
16 lobe
18 grip lever
20 rotor plate
22 opening
24 actuating slot
26 lobe
28 grip lever
30 sled
32 borehole
34 borehole
36 guide bolt
38 head
42 mounting pin
44 block
46 receptacle pocket
48 retractor valve
50 borehole
52 detent ball
54 compression spring
56 adjustment screw
58 detent recess
60 clamping bolt
62 eccentric lever
64 eccentric cam
66 mandrel
68 mandrel grip
70 support plate
72 shaft
74 end piece
76 circumference step
78 detent recess
80 widened segment
82 detent piece

The invention claimed is:

1. An anal retractor with retractor valves guided for movement apart, comprising:
   a base plate (10) with a central access opening (12);
   at least three guide slots (14) in the base plate (10) extending radially outside of the opening (12) and angularly offset relative to each other;
   retractor valves (48) radially displaceable in the guide slots (14), projecting generally perpendicularly from the base plate (10) in the distal direction;
   actuating means (20, 24) for radial displacement of the retractor valves (48) in the guide slots (14); and
   wherein the actuating means include a rotor plate (20) lying against the base plate (10), wherein the base plate (10) and the rotor plate (20) are rotatable concentrically relative to each other, wherein the rotor plate (20)

exhibits actuating slots (24) respectively intersecting the guide slots (14) of the base plate (10) and wherein the retractor valves (48) are displaceable by means of guide bolts (36) extending through the guide slots (14) and the actuating slots (24).

2. The anal retractor according to claim 1, wherein the guide slots (14) are provided offset relative to each other in equal angular spacing.

3. The anal retractor according to claim 2, wherein the guide slots (14) are offset from each other respectively by 90°.

4. The anal retractor according to claim 1, wherein sleds (30) are guided in the guide slots (14), and wherein the retractor valves (48) are releasably held in the sleds (30).

5. The anal retractor according to claim 4, wherein the retractor valves (48) are held releaseably locked in the sleds (30).

6. The anal retractor according to claim 1, wherein the guide bolts (36) are provided on sleds (30).

7. The anal retractor according to claim 1, wherein the base plate (10) and the rotor plate (20) are clampable relative to each other for fixing the position of the retractor valves (48).

8. The anal retractor according to claim 7, wherein the one of the guide bolts (36) is a tensioning bolt (60), which by means of a tensioning element (62, 64) is axially moveable, in order to press and clamp the base plate (10) and the rotor plate (20) against each other.

9. The anal retractor according to claim 8, wherein the tensioning element is an eccentric lever (62) mounted on the clamping bolt (60), which supports itself with an eccentric cam (64).

10. The anal retractor according to claim 1, wherein the base plate (10) and the rotor plate (20) are in the shape of a circular disk, which exhibit radially projecting grip levers (18, 24) on their outer circumference for actuation.

11. The anal retractor according to claim 1, wherein a mandrel (66) is introduced in the central access opening (12) of the base plate, which projects distally from the base plate (10) and has on its distal end a conical end piece (74), which with its proximal outer edge overlaps the distal ends of the retractor valves (48), when the retractor valves (48) are in their radial inner position.

12. The anal retractor according to claim 11, wherein the mandrel includes a pin (42), which is seat axially displaceably in a mandrel grip (68) proximal from the base plate (10).

13. The anal retractor according to claim 12, wherein a shaft (72) is ratchetedly engagable in the mandrel grip (68) in defined axial positions.

14. The anal retractor according to claim 1, wherein the guide slots (14) and/or actuating slots (24) includes widened segments (80), through which the guide bolt (36) can pass axially, in order to separate the base plate (10) and the rotor plate (20) from each other.

* * * * *